United States Patent [19]

Hesse

[11] Patent Number: Plant 6,551

[45] Date of Patent: Jan. 24, 1989

[54] CHRYSANTHEMUM PLANT NAMED 24-KARAT

[75] Inventor: Peter S. Hesse, Bradenton, Fla.

[73] Assignee: Ball Pan Am Plant Co., Parrish, Fla.

[21] Appl. No.: 56,982

[22] Filed: Jun. 3, 1987

[51] Int. Cl.[4] ..... A01H 5/00

[52] U.S. Cl. ..... Plt./78

[58] Field of Search ..... Plt./74–82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named 24-Karat, characterized by its decorative form and relatively large inflorescence, intense deep yellow flower color, upright growth habit, 9 week flowering response.

1 Drawing Sheet

The present invention comprises a new and distinct cultivar of *Chrysanthemum morifolium,* Ramat., hereinafter referred to by the cultivar name 24-Karat.

24-Karat is a product of a planned breeding program which had the objective of creating new Chrysanthemum cultivars having a compact, freely branching habit, 9 week flower response, orange-bronze decorative flower, and the ability to be grown in 4½" to 6½" pots. Such traits in combination were not present or needed improvement in previously available commercial cultivars.

24-Karat was originated from a hybridization made by Peter S. Hesse in a controlled breeding program in West Chicago, Ill. in 1980. The female parent was the cultivar British Gold. The male parent of 24-Karat was the cultivar Pot-O-Gold. 24-Karat was discovered and selected as one flowering plant within the progeny of the stated parentage by applicant in November 1981 in a controlled environment in Parrish, Fla.

The first act of asexual reproduction of 24-Karat was accomplished when vegetative cuttings were taken from the initial selection in February 1982 in a controlled environment in Parrish, Fla. by a technician working under formulations established and supervised by applicant. Horticultural examination of selected units initiated in May 1982 has demonstrated that the combination of characteristics as herein disclosed for 24-Karat are firmly fixed and are retained through successive generations of asexual reproduction.

The following traits have been repeatedly observed and are determined to be basic characteristics of 24-Karat, which in combination distinguish this Chrysanthemum as a new and distinct cultivar:

1. Intense deep yellow to almost yellow bronze flower color.
2. Nine (9) week flowering response.
3. Upright growth habit.
4. Less prone than normal to heat delay.
5. Decorative flower form.
6. Relatively large diameter of inflorescence.

24-Karat has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to 24-Karat is the commercial cultivar Mandalay. In comparison to Mandalay, 24-Karat has a lighter bronze flower color, 1 week earlier flower response, and its habit is more upright.

The accompanying photographic drawing shows typical inflorescence and foliage characteristics of 24-Karat. The photograph is in black and white, with a single flower being colored to accurately depict true flower color.

In the following description, color references are made to The Royal Horticultural Society Color Chart. The color values were determined at approximately 9:40 a.m. on Apr. 3, 1987 under fluorescent light at Parrish, Fla.

Classification:

*Botanical.*—*Chrysanthemum morifolium,* Ramat., cv. 24-Karat.

*Commercial.*—Decorative pot.

INFLORESCENCE

A. Capitulum:
- *Form.*—Flat.
- *Type.*—Double.
- *Diameter across face.*—75–90 mm.

B. Corolla of ray florets:
- *Color (general tonality from a distance of three meters).*—Orange-bronze.
- *Color (upper surface).*—13A.
- *Color (under surface).*—13B.

C. Corolla of disc florets:
- *Color (mature).*—Yellow.
- *Color (immature).*—Yellow.

D. Reproductive organs:
- *Androecium.*—Very few; present in disc florets only.
- *Gynoecium.*—Present in both disc and ray florets.

PLANT

A. General appearance:
- *Height.*—30–37 cm above the edge of the pot.

B. Foliage:
- *Color (upper surface).*—147A.
- *Color (under surface).*—147B.
- *Shape.*—Ovate and deeply lobed with double serrated leaf margins.

I claim:

1. A new and distinct cultivar of Chrysanthemum plant named 24-Karat, as illustrated and described, and particularly characterized by its decorative form and relatively large inflorescence, intense deep yellow flower color, upright growth habit, and its 9 week flowering response.

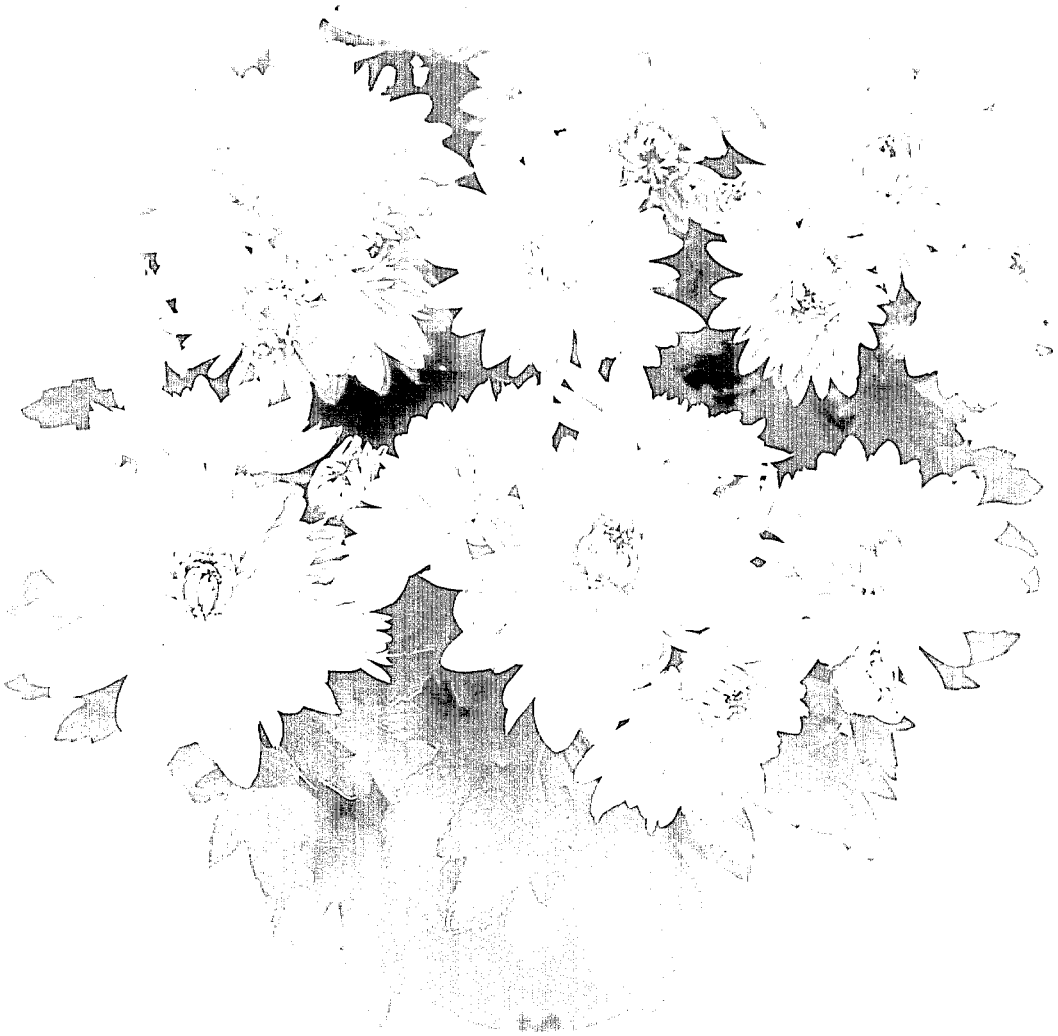

* * * * *